(12) United States Patent
Lee

(10) Patent No.: US 7,827,851 B2
(45) Date of Patent: Nov. 9, 2010

(54) PACKAGING STRUCTURE OF GAS DETECTOR AND METHOD FOR MAKING THE SAME

(75) Inventor: Tzong-Sheng Lee, Hsinchu (TW)

(73) Assignee: Unimems Manufacturing Co., Ltd., Hsinchu (TW)

( * ) Notice: Subject to any disclaimer, the term of this patent is extended or adjusted under 35 U.S.C. 154(b) by 1015 days.

(21) Appl. No.: 11/598,657

(22) Filed: Nov. 14, 2006

(65) Prior Publication Data
US 2007/0144903 A1 Jun. 28, 2007

(30) Foreign Application Priority Data
Dec. 27, 2005 (TW) ............... 94146810 A

(51) Int. Cl.
*G01N 27/00* (2006.01)
(52) U.S. Cl. .................................... 73/31.05
(58) Field of Classification Search ............ 73/23.2, 73/31.05
See application file for complete search history.

(56) References Cited

U.S. PATENT DOCUMENTS

| | | | | |
|---|---|---|---|---|
| 4,345,301 A | * | 8/1982 | Nelson | 361/782 |
| 5,247,827 A | * | 9/1993 | Shah | 73/28.01 |
| 5,396,796 A | * | 3/1995 | Kotani et al. | 73/431 |
| 5,721,430 A | * | 2/1998 | Wong | 250/339.13 |
| 5,729,207 A | * | 3/1998 | Yamano | 340/628 |
| 5,753,797 A | * | 5/1998 | Forster et al. | 73/24.01 |
| 6,067,840 A | * | 5/2000 | Chelvayohan et al. | 73/23.2 |
| 6,418,778 B1 | * | 7/2002 | Shiau | 73/23.23 |
| 6,756,793 B2 | * | 6/2004 | Hirono et al. | 324/690 |
| 7,043,958 B2 | * | 5/2006 | McGee et al. | 73/1.07 |
| 7,249,490 B2 | * | 7/2007 | Pendergrass | 73/31.05 |
| 7,540,183 B2 | * | 6/2009 | Komninos | 73/40.5 A |
| 7,541,587 B2 | * | 6/2009 | Cutler et al. | 250/339.13 |
| 7,553,071 B2 | * | 6/2009 | Legl et al. | 374/28 |
| 2006/0191318 A1 | * | 8/2006 | McBride et al. | 73/23.2 |
| 2008/0190174 A1 | * | 8/2008 | Kooi et al. | 73/31.01 |
| 2009/0151424 A1 | * | 6/2009 | Huang et al. | 73/23.2 |

FOREIGN PATENT DOCUMENTS

JP 04353753 A * 12/1992
WO WO 2004104523 A1 * 12/2004

* cited by examiner

*Primary Examiner*—John Fitzgerald
(74) *Attorney, Agent, or Firm*—Rosenberg, Klein & Lee

(57) ABSTRACT

The present invention provides a packaging structure of a gas detector and the method for making the same. The packaging structure of the gas detector includes a printed circuit board, a detection device and a ventilation cover. The detection device is attached to the printed circuit board by adhesive, and metallic wires are formed on the printed circuit board by wire-bonding process. The ventilation cover is positioned at the printed circuit board to cover the detection device. Signal terminals of the detection device are electrically connected with the contact terminals of the printed circuit board so as to test and check signals of the detection device. In this regard, the present invention is used to test and package a plurality of detection devices using one printed circuit board and without metallic terminals so that cost of the gas detector is significantly reduced.

2 Claims, 7 Drawing Sheets

PACKAGING STRUCTURE OF GAS DETECTOR AND METHOD FOR MAKING THE SAME

BACKGROUND OF THE INVENTION

1. Field of the Invention

The present invention relates to a packaging structure of a gas detector and the method for making the same, and in particular, to a packaging structure of a gas detector with semiconductor devices.

2. Description of Related Art

FIG. 1 illustrates a conventional gas detector 7. A cover 70 is positioned at a plastic base plate 72 and has a ventilation area 74. A detection device 71 is positioned and hung within the cover 70. The detection device 71 is respectively connected with two terminals 73 through two metallic wires 75, and the two terminals 73 penetrate through the plastic base plate 72 so that electrical signals from the detection device 71 are transmitted through the two terminals 73.

FIG. 2 illustrates another type of a conventional gas detector 8. A cover 80 is positioned at a metallic base plate 82 and has a ventilation area 85. A detection device 81 is positioned and hung within the cover 80. The detection device 81 is respectively connected with two terminals 83 through two metallic wires 86 so that electrical signals from the detection device 81 are transmitted through the two terminals 83. Each of insulation material 84 is formed between each of the two terminals 83 and the metallic base plate 82 so that the two terminals 83 are electrically insulated from the metallic base plate 82.

Two types of conventional gas detectors are described above. No matter what the base plate is made of plastic or metallic material, the detection device is hung within the gas detectors and electrical signals must be transmitted through the terminals. It is difficult to manufacture the conventional gas detectors in mass production so cost is high.

Thus, there is a need for a packaging structure of a gas detector and the method for making the same.

SUMMARY OF THE INVENTION

It is an object of the present invention to provide a packaging structure of a gas detector and the method for making the same. According to the present invention, the packaging structure utilizes a printed circuit board instead of the plastic base plate or the metallic base plate. In addition, the terminals of the prior art are omitted so that cost and difficulty of packaging are significantly reduced.

To achieve object of the present invention, the present invention provides a packaging structure of a gas detector. The packaging structure of the gas detector includes a printed circuit board, contact terminals, a detection device and a ventilation cover. The contact terminals and the detection device are disposed on the printed circuit board. Signal terminals of the detection device are electrically connected with the contact terminals. The ventilation cover is positioned at the printed circuit board to cover the detection device.

Another object of the present invention provides a method for making a packaging structure of a gas detector. The method includes steps: providing a printed circuit board including a plurality of overlapping contact terminals; attaching the overlapping contact terminals to corresponding detection devices and connecting terminals of the detection devices with the overlapping contact terminals by wire bonding process; and providing a plurality of ventilation covers to cover corresponding the detection devices.

According to the present invention, the detection devices are attached to the printed circuit board and terminals are replaced with electrical terminal copper foils. In addition, a plurality of detection devices are packaged in one printed circuit board so that the packaging structure of a gas detector can be manufactured in mass production. In this regard, the packaging structure of the gas detector of the present invention can be manufactured in mass production without metallic base or plastic base.

BRIEF DESCRIPTION OF THE DRAWINGS

The present invention can be fully understood from the following detailed description and preferred embodiment with reference to the accompanying drawings, in which.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

Figure 1:
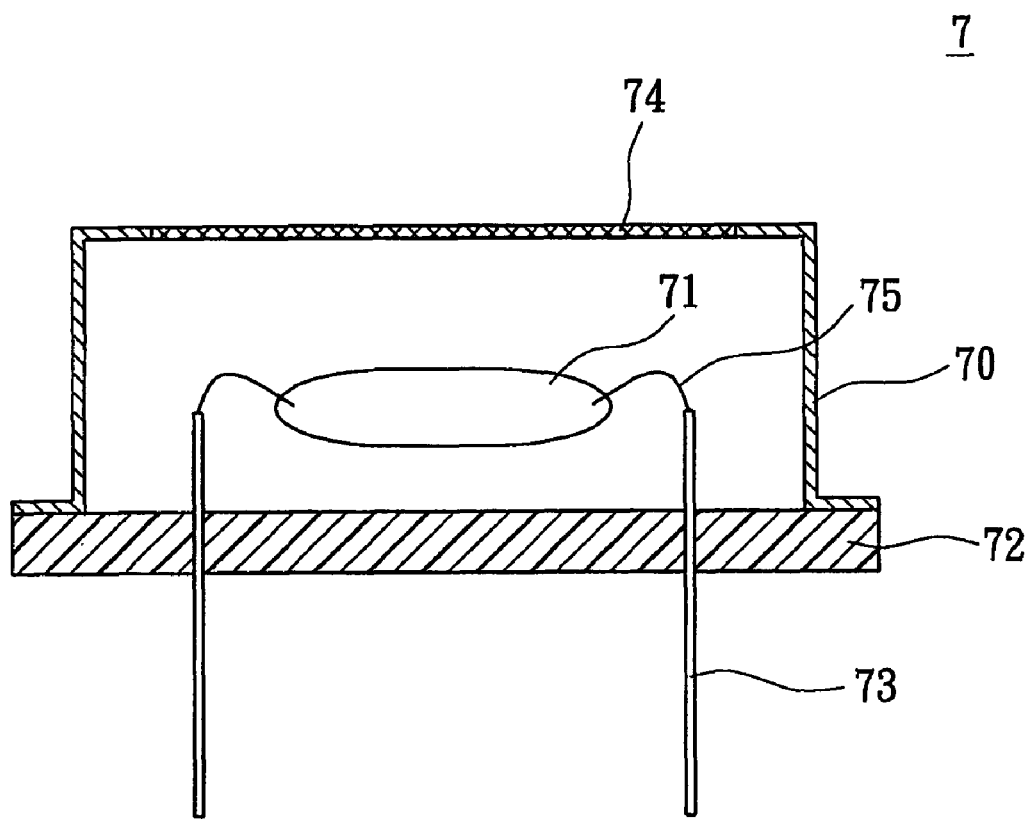
FIG. 1 is a cross section of a gas detector in the prior art.
Figure 2:
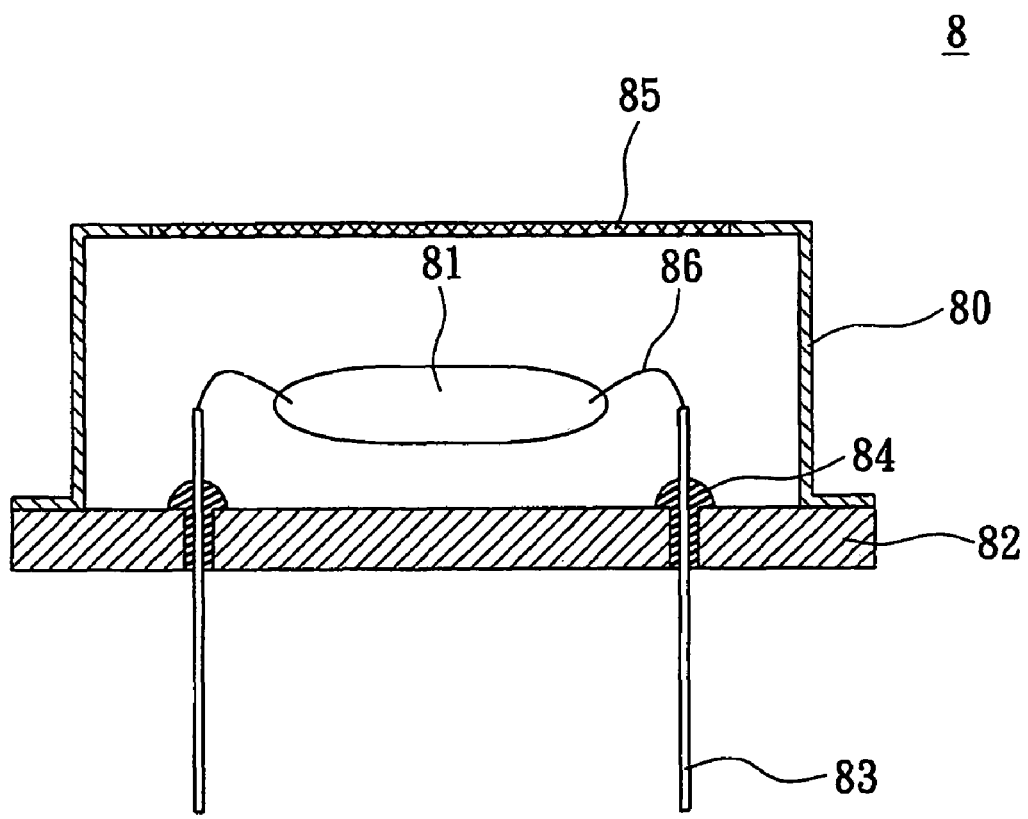
FIG. 2 is a cross section of another type of gas detector in the prior art.
Figure 3:
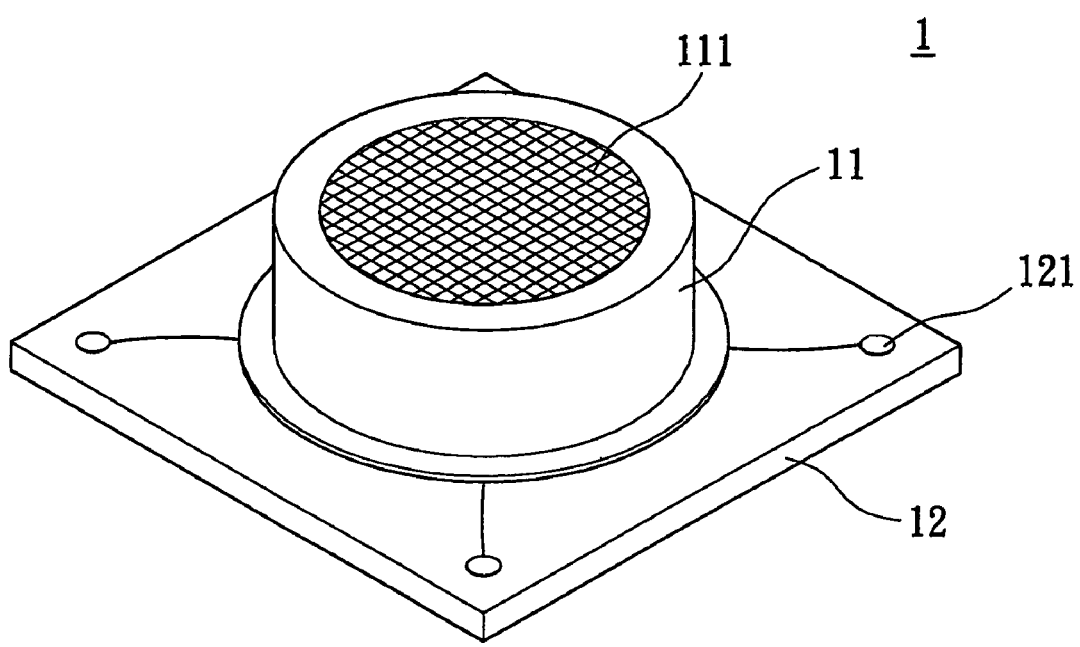
FIG. 3 is a perspective view of a gas detector according to one embodiment of the present invention.

Reference is made to FIG. 3. FIG. 3 illustrates a perspective view of a gas detector 1 according to one embodiment of the present invention. The gas detector 1 of the present invention utilizes semiconductor devices to detect gas. The packaging structure of the gas detector 1 includes a printed circuit board 12 and a ventilation cover 11, and components related with gas detection is covered by the ventilation cover 11. The ventilation cover 11 is ventilative because a ventilation area 111 is positioned at the ventilation cover 11 and a plurality of holes.

Figure 4:
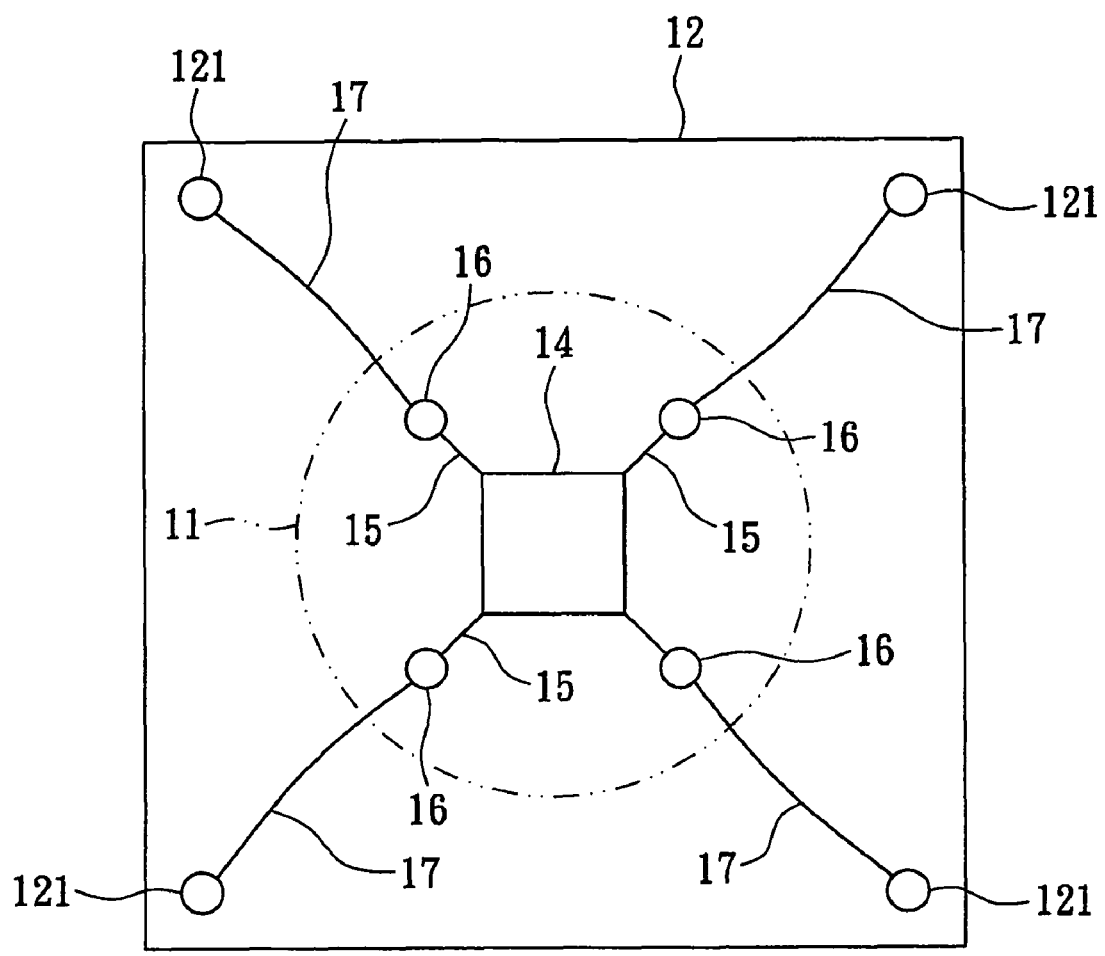
FIG. 4 is a top plan view of a gas detector without a ventilation cover according to the present invention.

Reference is made to FIG. 4. FIG. 4 illustrates structure within the ventilation cover 11. A detection device 14 is disposed on front surface of the printed circuit board 12 and has a plurality of first contact terminals 16 in its circumference. Each of the first contact terminals 16 is electrically connected with the signal terminals of the detection device 14 by conductive wires 15. A plurality of through holes 121 are disposed in the circumference of the printed circuit board 12 and are plated with conductive material so that each of the through holes 121 is electrically connected with corresponding the first contact terminal 16 through the conductive wire 17.

Figure 5:
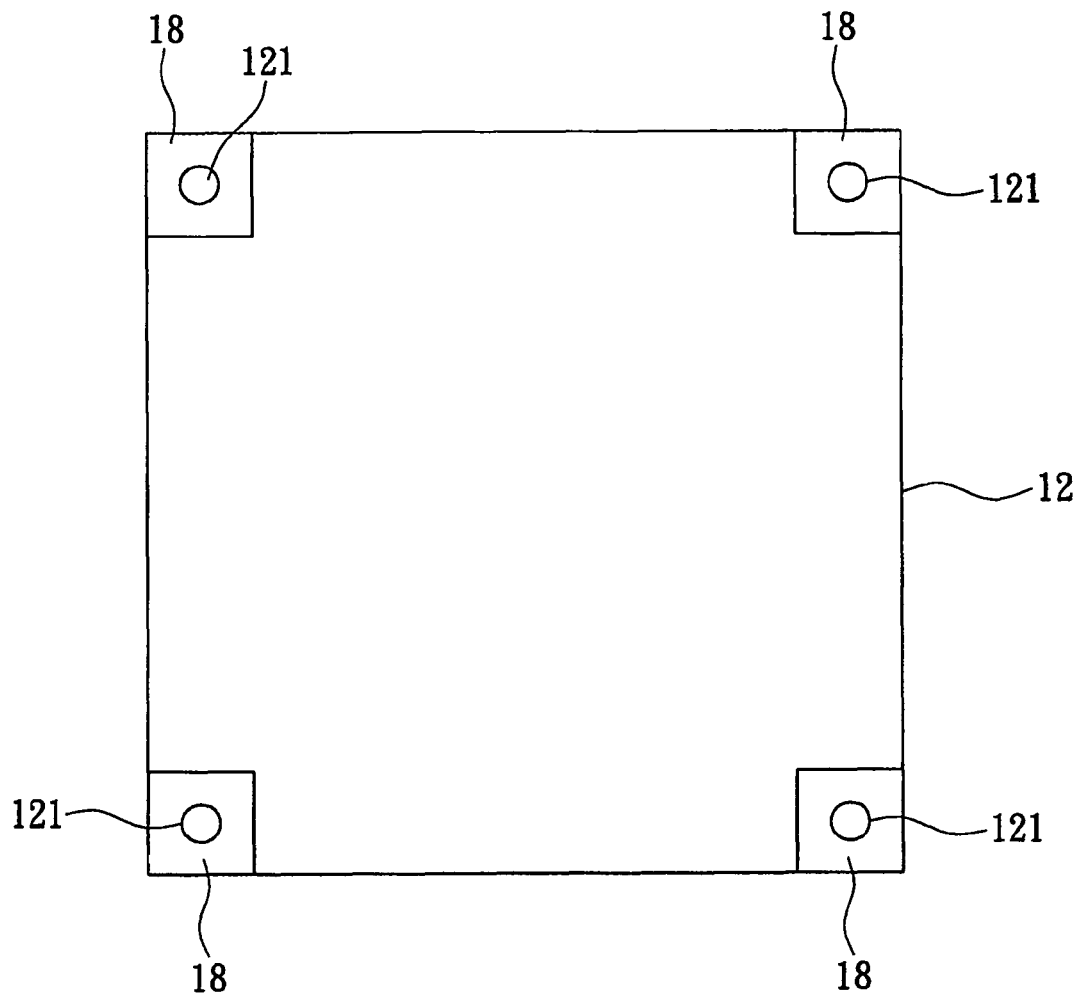
FIG. 5 is a bottom plan view of a gas detector according to the present invention.

Reference is made to FIG. 5. A plurality of second contact terminals 18 are disposed at the rear surface of the printed circuit board 12, and each of the second contact terminals 18 is electrically connected with corresponding the through hole 121. In this regard, the first contact terminals 16 are electrically connected with the second contact terminals 18. Signals from the signal terminals of the detection device 14 are transmitted through the first contact terminals 16 or the second contact terminals 18.

According to the present invention, the detection device 14 utilizes semiconductor devices to detect gas. The first contact terminals 16 are wire-bonding pads of the detection device 14, and the second contact terminals 18 are wire-bonding pads of external circuits. The conductive wires 15 are chip-bonding wires, and the conductive wires 17 are made of copper foil and disposed at the printed circuit board 12.

Figure 6:
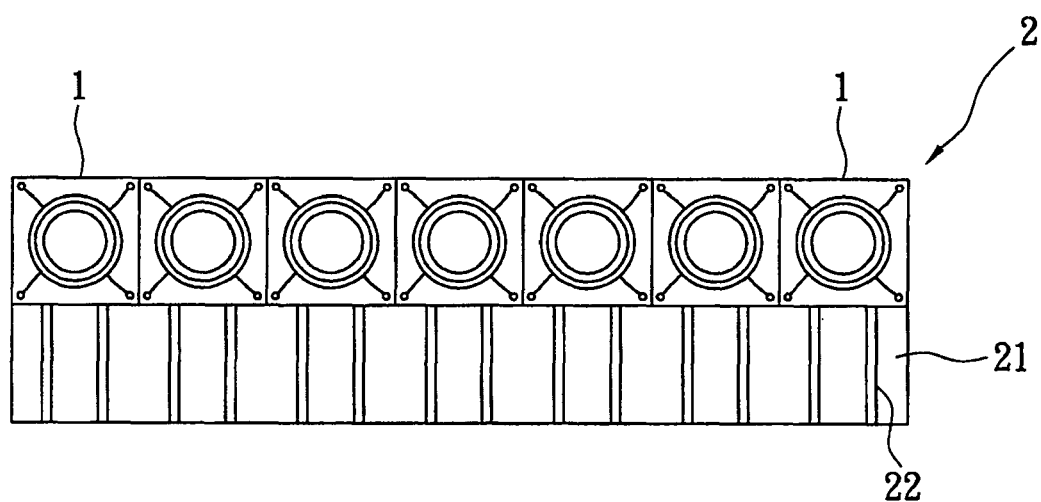
FIG. 6 is a plan view of a gas detection module according to the present invention.

Reference is made to FIG. 6. According to the present invention, the gas detector 1 utilizes printed circuit boards instead of metallic base plates or plastic base plates. When the gas detectors 1 are subjected to packaging process, a plurality of gas detectors 1 are positioned at one printed circuit board so that a gas detection module 2 is formed. The gas detection module 2 includes a test portion 21 having a plurality set of test wires 22. Each of the gas detectors 1 correspond with each of the test wires 22. Each of the test wires 22 is electrically connected with the first contact terminals 16 or the second contact terminals 18. The test wires 22 are used to check related signals of the gas detectors 1 before the gas detectors 1 are shipped to customers. When the test is completed, the test portion 21 of the gas detection module 2 is removed so that the gas detectors 1 in series or single gas detector 1 are formed and shipped.

Figure 7:
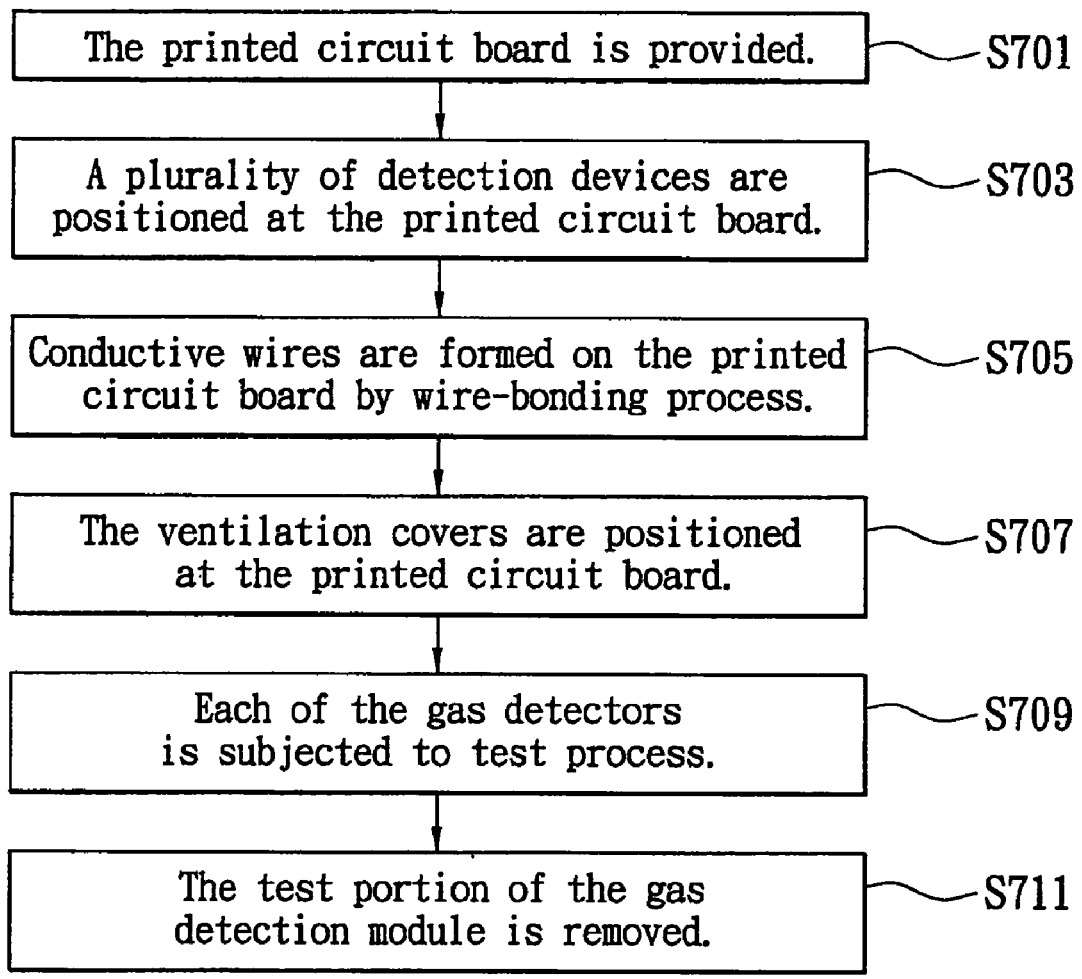
FIG. 7 is a flowchart of a method for making a packaging structure of a gas detector according to the present invention.

Reference is made to FIG. 7. FIG. 7 illustrates a flowchart of a method of the present invention. The gas detection module 2 as shown in FIG. 6 is manufactured by the method of the present invention. The processing of the flowchart is described in detail below.

Step S701: In step S701, the printed circuit board 12 is provided. Then, processing goes to step S703.

Step S703: In step S703, a plurality of detection devices 14 are positioned at the printed circuit board 12 by die-bonding process. Then, processing goes to step S705.

Step S705: In step S705, conductive wires 15 are formed on the printed circuit board 12 by wire-bonding process and electrically connected with the detection devices 14. Then, processing goes to step S707.

Step S707: In step S707, according to manufacturing techniques of the printed circuit board 12, the conductive wires 17, the first contact terminals 16, the second contact terminals 18, the through holes 121 or the test wires 22 are formed at the printed circuit board 12. The ventilation covers 11 are positioned at the printed circuit board 12. Then, processing goes to step S709.

Step S709: In step S709, each of the ventilation covers 11 is used to cover each of the gas detectors 1. Adhesive is applied to the area in the vicinity of each of the detection devices 14, and the ventilation covers 11 are then positioned at the printed circuit board 12 and includes a ventilation area 111. Each of the gas detectors 1 is subjected to test process through the test wires 22. Then, processing goes to step S711.

Step S711: In step S711, when the test process is completed, the test portion 21 of the gas detection module 2 is removed so that the gas detectors 1 in series or single gas detector 1 are formed and shipped. Then, the processing stops.

As described above, advantages of the present invention are in the following.

1. The gas detectors utilize the printed circuit boards as base plates and electrical circuits are formed on the printed circuit boards. In this regard, signals of the detection devices are output to the front surface and the rear surfaces of the printed circuit boards without additional terminals from the detection devices. Cost of manufacturing is significantly reduced.

2. The gas detector of the present invention is different from that of prior art. According to the present invention, a plurality of gas detectors are positioned at one printed circuit board and are subjected to test process before shipping. It saves much times and cost of test device is reduced.

While the invention has been described with reference to the preferred embodiments, the description is not intended to be construed in a limiting sense. It is therefore contemplated that the appended claims will cover any such modifications or embodiments as may fall within the scope of the invention defined by the following claims and their equivalents.

What is claimed is:

1. A packaging structure of a gas detector, comprising:
   a printed circuit board;
   a plurality of first contact terminals, disposed on the front surface of the printed circuit board;
   a plurality of second contact terminals, disposed on a rear surface of the printed circuit board, and electrically connected with the first contact terminals by through holes and conductive wires made of a copper foil, the second contact terminals being in spatially unregistered relation to the first contact terminals;
   a semiconductor device, operable to detect a gas disposed on the front surface of the printed circuit board and signal terminals of the semiconductor device electrically connected with the first contact terminals by chip-bonding wires, wherein the first contact terminals are wire-bonding pads of the semiconductor device, while the second contact terminals are wire-bonding pads of external circuits external to the packaging structure; and
   a ventilation cover, positioned at the printed circuit board to cover the semiconductor device.

2. The packaging structure of a gas detector as claimed in claim 1, wherein the ventilation cover includes a plurality of holes.

* * * * *